United States Patent [19]

Pelham et al.

[11] Patent Number: 4,521,407

[45] Date of Patent: Jun. 4, 1985

[54] TREATMENT OF ACQUIRED IMMUNE DEFICIENCY SYNDROME WITH THYMUS EXTRACT

[75] Inventors: Russell W. Pelham, E. Weymouth; Charlotte S. Redden, Natick, both of Mass.; Aliza Eshkol, Tel-Hashomer, Israel; Gerald E. Stiles, Duxbury, Mass.

[73] Assignee: Serono Pharmaceutical Partners, Randolph, Mass.

[21] Appl. No.: 527,569

[22] Filed: Aug. 29, 1983

[51] Int. Cl.³ ............................................. A61K 35/26
[52] U.S. Cl. ..................................................... 424/95
[58] Field of Search ......................................... 424/95

[56] References Cited

PUBLICATIONS

Trainin et al—Chem. Abst., vol. 95, (1981), p. 22618w.

*Primary Examiner*—Sam Rosen
*Attorney, Agent, or Firm*—Ostrolenk, Faber, Gerb & Soffen

[57] ABSTRACT

The cellular immune system of a person having acquired immune deficiency syndrome is stimulated by administering an immunopotentiating effective amount of a calf thymus extract to such person, the extract showing, upon electrophoresis on polyacrylamide gel at pH 8.6 two main characteristic bands with an Rf of about 0.25 and 0.44.

8 Claims, No Drawings

TREATMENT OF ACQUIRED IMMUNE DEFICIENCY SYNDROME WITH THYMUS EXTRACT

BACKGROUND OF THE INVENTION

Primary immunodeficiency is a very rare, but devastating, condition in which there is a partial or total collapse or absence of one or more classes of immune responses. It is typified by recurrent or chronic life-threatening infections and by the necessity for its victims to live in rigorously controlled, sterile conditions. There is no existing treatment other than isolation of the patient from all potential sources of infection.

In secondary immunodeficiency, the immune system function is reduced and may appear as a result of age, disease or the use of certain therapies, such as cytostatic radiotherapy or chemotherapy for cancer. Patients whose immune system function is reduced are vulnerable to both viral and other infections, and treatment of such infections may be complicated and/or protracted.

Acquired immune deficiency syndrome (AIDS) is a recently identified syndrome in which a person's immune system after functioning normally ceases to function adequately. While AIDS resembles somewhat the clinical pathology of secondary immunodeficiency, it alone is uniquely characterized by a reduced ratio of helper to suppressor T-cell subsets.

The etiology of acquired immune deficiency syndrome is unknown and no effective treatment has yet been found. Because of the breakdown in the immune system, such individuals are highly vulnerable to infections and there has been a high mortality from opportunistic infections and Kaposi's sarcoma. See, e.g. "Immunocompromised Homosexuals" (Editorial) Lancet 1981; ii: 1325-6; Center for Disease Control, "Epidemiological Aspects of the Current Outbreak of Kaposi's Sarcoma and Opportunistic Infections", N. Engl. J. Med. 1982, 306: 248-52; Gerstoft et al., "Severe Acquired Immunodeficiency in European Homosexual Men", Br. Med. J. 1982, 285: 17-19. The two year mortality rate has been reported to be as high as 80%.

It has been known for some time that the thymus gland is connected with the immune functions of the body and therefore great interest has been indicated in substances which have been isolated from the thymus. Certain lymphocytes are differentiated within the thymus and leave as thymus derived cells, called T-cells, which circulate in the blood, to the lymph, spleen and lymph nodes. See, e.g., U.S. Pat. Nos. 4,002,602, 4,010,148, 4,082,737, 4,148,886 and 4,167,557. Attempts to restore cell mediated immunity by reviving the thymus dependent T-cell functions have been carried out in experimental animals and in humans by using several thymic extracts of different chemical, physical and biological activities. Bach, "Thymic Hormones: Biochemistry and Biological and Clinical Activity", Ann. Rev. Pharmacol. Toxicol., 17, 281 (1977); Trainin, "The Role of Thymic Hormones in Regulation of the Lymphoid System", in Loor et al (Eds.), B and T Cells in Immune Recognition (Wiley & Sons, London) 83-102 (1977). It has been observed that highly purified thymic factors are probably incapable of inducing in immunodeficient animals a T-cell dependent immune response body in vitro and in vivo. Masuda, V. "Abstract from the Symposium on "Immunodeficiency, its Nature and Etiological Significance in Human Disease", Tokyo, Sept. 13-15, 1976. This observation seems to support the assumption that several protein hormones contained in a thymic extract are required in order to achieve a proper range of activity.

It has now been discovered that a particular thymic extract, hereinafter referred to as TP-1, can successfully be used in stimulating the cellular immune system of a person having acquired immune deficiency syndrome. This discovery is particularly surprising because the etiology and prophylaxis of acquired immune deficiency syndrome is not known.

It is, therefore, the object of this invention to provide a method of stimulating the cellular immune system in a person having acquired immune deficiency syndrome. This and other objects of the invention will become apparent to those skilled in this art from the following detailed description.

SUMMARY OF THE INVENTION

This invention relates to the treatment of acquired immune deficiency syndrome and more particularly to a method of stimulating the cellular immune system in a person having acquired immune deficiency syndrome by administering to such person an immunopotentiating effective amount of a calf thymus hormone extract, TP-1, which extract shows, upon electrophoresis on polyacrylamide gel at pH 8.6, two main characteristic bands with a Rf of about 0.25 and 0.44.

DESCRIPTION OF THE INVENTION

TP-1 is a known calf thymus extract which has been described, inter alia, in Falchetti, et al., "Isolation, Partial Characterization and Biological Effects of a Calf Thymus Factor", Abstracts of Third European Immunology Meeting, Copenhagen, Aug. 25-27, 1976; Falchetti, et al., "Pharmacological and Biological Properties of a Calf Thymus Extract (TP-1)", Drugs Exptl. Clin. Res. 3 (2) 39-47 (1977); Bergesi, et al., "Chemical Characterization and Biological Activity of a New Thymic Extract", Folia Allergol. Immunol. Clin. 21: 201, (1977); and Falchetti, et al., "Bioassay for Thymic Extracts: Guinea Pig Spleen Lymphocytes—Rapid Red Blood Cells Rosette Method", Cancer Biochem. Biophys. Vol. 4, pp. 69-74 (1979). TP-1 is manufactured by Serono Laboratories, Inc.

The extraction and purification of TP-1 is described in the Bergesi, et al. article as follows: calf thymuses, accurately homogenized, were extracted with ammonium acetate 0.15M. and centrifuged in the presence of decalcite. The liquid thus obtained was collected and heated at 70° C. for 30 minutes. The proteins coagulated using this procedure were separated by filtration and the clear liquid was precipitated by the addition of ammonium sulfate until a 45% saturation had been achieved. The clear liquid obtained, after separation of the precipitate via centrifugation, was brought to 90% saturation with ammonium sulfate. The precipitate from this last pass was collected by filtration, dissolved in water and ultrafiltered across a PM-10 membrane. The ultrafiltrate containing salts and protein matter with a molecular weight lower than about 10,000 was then lyophilized, desalted on Sephadex G-25 and subsequently gel-filtered on Sephadex G-50. Collected were the fractions which, on electrophoresis in polyacrylamide gel at pH 8.6, showed two characteristic bands with an Rf of about 0.25 and 0.44 compared with bromophenol blue used as a tracer.

TP-1 has been found to have the capacity to increase the responsiveness of mouse spleen lymphoid cells to phytohaemoagglutinin (PHA) and to concanavalin A stimulation, while it did not increase the response to lipopolysaccharide stimulation; to stimulate an increase in E-rosette forming lymphocytes from human cord blood, to increase the percentage of Theta-positive cells of the mouse spleen population and to stimulate the capacity of allogeneic mouse marrow cells to induce a graph v. host response in X-ray irradiated mice. TP-1 did not cause any acute toxic effect or noticeable side effects in doses of up to 100 mg./kg. when administered intraperitoneally to mice for 21 days or to rats for 31 days nor when administered subcutaneously to rats for 180 days in doses up to 50 mg./kg., nor in dogs receiving intramuscular doses up to 10 mg./kg. for 180 days. It did not alter the neuromuscular transmission as evaluated in vitro on the rate phrenic diaphragm nerve and in vivo on the mouse tibial muscle, nor the blood pressure, the electrocardiographic and pneumographic pattern.

TP-1 can easily be differentiated from other thymic extracts because it has two main characteristic bands upon electrophoresis on a polyacrylamide gel at pH 8.6 while other thymic extracts presently known show only a single characteristic band. At pH 8.6, TP-1's two bands are at Rf=0.25 ±0.05 and Rf=0.45±0.05.

To the present, TP-1 has been administered principally by intramuscular injection although other modes of administration can also be employed. The pharmaceutical preparations contain an immunopotentiating effective amount of TP-1 together with a compatible, pharmaceutically acceptable carrier or diluent which, in case of the intramuscular formulation, can be sterile water. Other conventionally employed excipients such as mannitol can also be included, and the usual array of excipients can be employed in other administration forms. It is presently preferred that the intramuscular formulations contain about 5 to 25 mg. protein per ml.

The immunopotentiating effective amount of TP-1 is dependent on the age and weight of the individual being treated, the mode of administration and the presence or absence of opportunistic infection, Kaposi's sarcoma or other disease. While the dosage administered per day can typically be in the range of about 0.5 to about 1.0 mg./kg., the response varies considerably from individual to individual and is therefore best determined by the attending clinician.

TP-1 was studied in vitro by incubation with blood samples from various patients having diagnosed acquired immune deficiency syndrome and various control patients' blood samples. The first study was for phytohemoagluttin stimulation (PHA). This method is based on the fact that peripheral blood lymphocytes in the presence of monocytes divide when stimulated by PHA and dividing cells are thymic derived lymphocytes. The extent of division can be quantified by measuring incorporation of $^3$H-thymidine into cellular DNA. After counting lymphocytes contained in serum free Hanks Balanced Salt Solution (HBSS) and removing those cells for T-cell rosette assay, the remainder of the cells are resuspended in a supplemented media (RPMI-1640 containing 25 mM Hepes Buffer) at a concentration of $2 \times 10^6$/ml. Cell aliquots are added to 10 ul. of the appropriate PHA dose (0.5 ug., 2 ug. or 10 ug.)/ml of lymphocyte suspension. $4 \times 10^5$ cells per aliquot are added, in triplicate, and are incubated for 72 hours at 37° C. in 5% $CO_2$ humidified atmosphere, labeled with 0.5u Ci$^3$H-methyl-thymidine and incubated for an additional 4.5 hours. The cells are then harvested and spread on a grid having a volume of $10^{-4}$ ml. The mean stimulation value recorded is the maximum of the three PHA doses. The results are shown in the following table:

| Incubating Substance | Dose, mcg. | A.I.D.S. Patient #1 | % Incr. | A.I.D.S. Patient #2 | % Incr. | A.I.D.S. Patient #3 | % Incr. |
|---|---|---|---|---|---|---|---|
| None | 0 | 94 | — | 53 | — | 145 | — |
| PHA | — | 103 | — | 99 | — | 25588 | — |
| TP-1 + PHA | 10 | 65 | −422 | 66 | −72 | 21170 | −17 |
| TP-1 + PHA | 50 | 104 | 11 | 112 | 28 | 33226 | 30 |
| TP-1 + PHA | 100 | 167 | 711 | 116 | 37 | 23115 | −10 |
| TP-1 + PHA | 250 | 113 | 111 | 154 | 120 | 18603 | −27 |
| Max. % Incr. | | 711 | | 119 | | 30 | |

In control studies, two individuals showed negative percent increases at all doses of TP-1 and four individuals showed positive increases (maximum 16, 20, 7 and 36%, respectively) although each had negative increases at 250 mcg. The fourth of such controls also had a negative increase at 10 mcg.

A second study was carried out for allogeneic stimulation. The basis of this study is the fact that peripheral blood lymphocytes in the presence of monocytes divide when stimulated by allogeneic (foreign) cells and the rate of division can be measured by quantification of radiolabled thymidine uptake into DNA. After counting the lymphocytes contained in serum free HBSS, and removal of those cells for T-cell rosette assay, the remainder are resuspended in the supplemented media at a concentration of $2 \times 10^6$/ml. An aliquot of control cells is irradiated with 3,000 rads. For each culture, $2 \times 10^5$ responding cells (in 0.1 ml) are mixed with sterile $2 \times 10^5$ stimulator irradiated cells (in 0.1 ml), in triplicate. The cultures are incubated for approximately 120 hours at 37° C. in 5% $CO_2$ humidified atmosphere, labeled with 0.5u Ci$^3$H-methyl thymidine, in 50 ul phosphate buffered saline and reincubated for an additional 18-24 hours. The cells are then harvested and counted. See Wara et al., New England Journal of Medicine, 1975, 292.780. The results are shown in the following table:

| Incubating Substance | Dose, mcg. | A.I.D.S. Patient #1 | % Incr. | A.I.D.S. Patient #2 | % Incr. |
|---|---|---|---|---|---|
| None | — | 185 | — | 234 | — |
| MLC | — | 330 | — | 929 | — |
| TP-1 + MLC | 10 | 605 | 190 | 648 | −40 |
| TP-1 + MLC | 50 | 498 | 116 | 399 | −76 |
| TP-1 + MLC | 100 | 387 | 39 | 426 | −72 |
| TP-1 + MLC | 250 | 575 | 169 | 840 | −13 |
| Max. % Incr. or Min. % Inhib. (−) | — | 190 | | −13 | |
| Max. % Inhib. (−) or Min. % Incr. | — | 39 | | −76 | |

The results of control studies with the sera of five individuals who did not have acquired immune deficiency syndrome, were:

|  | Control Patients | | | | |
| --- | --- | --- | --- | --- | --- |
|  | 1 | 2 | 3 | 4 | 5 |
| Max. % Incr. or Min. % Inhib. (−) | 12 | 16 | 30 | 6 | 70 |
| Max. % Inhib. (−) or Min. % Incr. | −43 | 4 | 18 | −11 | −23 |

TP-1 has been used in vivo to treat a 43 year old male having acquired immune deficiency syndrome. The individual was first seen in January, 1981 complaining of rash, malaise, alopecia and weight loss of one year's duration. Examinations showed ichthyosis, alopecia and lymphadenopathy. A year of intensive investigation followed but a firm diagnosis was not made until late 1981 when lymphocyte marker studies showed T-cell lymphopenia with an abnormal OKT4: OKT8 ratio. OKT4 and OKT8 are monoclonal antibodies specific to T-cell subsets, namely the human inducer/helper T-lymphocyte subclass and the human suppressor/-cytotoxic T-lymphocyte subclass, respectively. This, in combination with abnormal immunoglobulin concentrations, [IgA 7.6 g/l. (normal range 0.5-3 g/l) IgM 3.3 g/l (normal range 0.5-1.7 g/l) and IgG 8.3 g/l (normal range 5-16 g/l)] and results of liver function tests (aspartate transaminase activity periodically raised to 73 IU/l (normal range 17-35 IU/l)), plus the clinical picture, gave rise to the diagnosis.

In March, 1982, the patient developed fever, rigors, breathlessness and a cough. Chest radiography showed widespread infiltrates. The patient refused to undergo bronchoscopy and Pneumocystis carinii pnemonia was diagnosed clinically. Parental co-trimoxazole was started (20 mg. trimethoprim/kg. and 100 mg. sulphamethoxazole/kg.) and the patient improved. Overnight incubation in vitro of the patient's lymphocytes with TP-1 at a concentration of 100 mg./l induced a normal proportion of OKT4+ cells thereby providing a basis for the use of TP-1 in vivo. Accordingly, 0.75 mg. TP-1/kg. was started on alternate days intramuscularly shortly after the co-trimoxazole. Cytomegalovirus infection was sought and the virus subsequently isolated repeatedly from throat washings and urine.

On March 17, the number of OKT4+ cells was $15 \times 10^4/l$ and the number of cells increased to $100 \times 10^4/l$ on April 16 and to $121 \times 10^4/l$ on April 23. Between Apr. 23 and May 5, 1982, the patient was diagnosed to have candidiasis. Treatment with TP-1 was stopped after two months, by which time the lymphocyte count had dropped to pretreatment values. The patient died in June of an encephalitic illness resistant to chemotherapy, including antiviral agents. The failure of the immunostimulation to sustain lymphocytosis is probably attributable to his severe morbidity.

Various changes and modifications can be made in the process of the present invention without departing from the spirit and scope thereof. The various embodiments which have been described herein were for the purpose of further illustrating the invention but were not intended to limit it.

What is claimed is:

1. A method of stimulating the cellular immune system in a person having acquired immune deficiency syndrome by administering to such person an immunopotentiating effective amount of a calf thymus extract, which extract shows, upon electrophoresis on polyacrylamide gel at pH 8.6, two main characteristic bands with an Rf of about 0.25 and 0.44.

2. The method of claim 1, wherein the calf thymus extract is administered parenterally.

3. The method of claim 2, wherein the calf thymus extract is administered intramuscularly.

4. The method of claim 3, wherein the intramuscular administration unit dose contains about 5 to about 25 mg. protein per ml.

5. The method of claim 4, wherein the amount of calf thymus extract administered per day is in the range of about 0.5 to about 1.0 mg./kg.

6. The method of claim 1, wherein the administration unit dose contains about 5 to about 25 mg. protein per ml.

7. The method of claim 6, wherein the amount of calf thymus extract administered per day is in the range of about 0.05 to about 1.0 mg./kg.

8. The method of claim 1, wherein the amount of calf thymus extract administered per day is in the range of about 0.5 to about 1.0 mg./kg.

* * * * *